United States Patent [19]

Woodin, Jr. et al.

[11] Patent Number: 5,219,558

[45] Date of Patent: Jun. 15, 1993

[54] PHOTOPROTECTION COMPOSITIONS HAVING IMPROVED SUBSTANTIVITY

[75] Inventors: Frederick W. Woodin, Jr., Naugatuck; George E. Deckner, Trumbull, both of Conn.

[73] Assignee: Procter & Gamble, Cincinnati, Ohio

[21] Appl. No.: 824,965

[22] Filed: Jan. 22, 1992

Related U.S. Application Data

[63] Continuation of Ser. No. 428,219, Oct. 27, 1989, abandoned.

[51] Int. Cl.$^5$ ............................ A61K 7/42; A61K 7/44; A61K 7/48
[52] U.S. Cl. ........................................ 424/59; 424/60; 514/844; 514/847; 514/938
[58] Field of Search ..................... 424/59, 60

[56] References Cited

U.S. PATENT DOCUMENTS

| | | | |
|---|---|---|---|
| 3,915,921 | 10/1975 | Schlatzer, Jr. | 260/17.4 |
| 4,049,792 | 9/1977 | Elsnau | 424/66 |
| 4,120,948 | 10/1978 | Shelton | 424/64 |
| 4,172,122 | 10/1979 | Kubik et al. | 424/59 |
| 4,509,949 | 4/1985 | Huang et al. | 586/558 |
| 4,597,963 | 7/1986 | Deckner | 424/59 |
| 4,663,155 | 5/1987 | Murray et al. | 424/59 |
| 4,663,157 | 5/1987 | Brock | 424/59 |
| 4,699,780 | 10/1987 | Jennings et al. | 424/59 |
| 4,781,914 | 11/1988 | Deckner | 424/59 |
| 4,810,489 | 3/1989 | Murray et al. | 424/59 |
| 4,820,508 | 4/1989 | Wortzman | 424/59 |
| 4,894,222 | 1/1990 | Matravers et al. | 424/59 |
| 4,897,259 | 1/1990 | Murray et al. | 514/938 |

FOREIGN PATENT DOCUMENTS

| | | | |
|---|---|---|---|
| 255157 | 6/1987 | European Pat. Off. | 424/59 |
| 2217987 | 11/1989 | United Kingdom . | |

OTHER PUBLICATIONS

Soap/Cosmetics/Specialities, "Hydrophobically Modified 'Carbopol' Resins", May 1987.
Cosmetics & Toiletries, "A New Waterproofing Agent for Sunscreen Products", vol. 102, No. 3, p. 107, Mar. 1987.
Cosmetics & Toiletries, "Novel Cosmetic Emulsions", vol. 101, No. 11, p. 125, Nov. 1986.

Primary Examiner—Dale R. Ore
Attorney, Agent, or Firm—David K. Dabbiere; Anthony D. Sabatelli; Douglas C. Mohl

[57] ABSTRACT

Disclosed are topical compositions having improved substantivity such as improved water-proofing (e.g., resistance to perspiration) and rub-off resistance useful for protecting the skin from the harmful effects of ultraviolet irradiation, such as sunburn and sun-induced premature aging of the skin.

15 Claims, No Drawings

PHOTOPROTECTION COMPOSITIONS HAVING IMPROVED SUBSTANTIVITY

This is a continuation of application Ser. No. 428,219, filed on Oct. 27, 1989, now abandoned.

TECHNICAL FIELD

This invention relates to improved topical compositions having improved substantivity such as improved water-proofing (e.g., resistance to perspiration) and rub-off resistance useful for protecting the skin from the harmful effects of ultraviolet irradiation, such as sunburn and sun-induced premature aging of the skin.

BACKGROUND OF THE INVENTION

The damaging effects of sunlight on skin are well documented. Contrary to what most people believe, it is not necessary that one sunbathe to suffer the ill-effects of excessive UV exposure. In fact, a lot of damage can be done just by routine day-to-day activities in the sunlight. Some scientists estimate that over 70 percent of the damage the sun inflicts on the average person's skin over a lifetime is the result of simply being outdoors or even sitting by a window.

The major short term hazard of prolonged exposure to sunlight is erythema (i.e. sunburn). The 290 to 320 nanometer wavelength ultraviolet radiation range, designated as the "UVB" wavelength range, tends to be the primary cause of erythema. The 320 to 400 nanometer wavelength ultraviolet radiation range, designated as the "UVA" wavelength range, also produces erythema.

In addition to the short term hazard or erythema, there are also long term hazards associated with UV radiation exposure. One of these long term hazards is malignant changes in the skin surface. Numerous epidemiologic studies demonstrate a strong relationship between sunlight exposure and human skin cancer.

Another long term hazard of ultraviolet radiation is premature aging of the skin. This condition is characterized by wrinkling and yellowing of the skin, along with other physical changes such as cracking, telangiectasis (spider vessels), solar keratoses (growths), ecchymoses (subcutaneous hemorrhagic lesions), and loss of elasticity (sagging). The adverse effects associated with exposure to UVA and UVB wavelength radiation are more fully discussed in DeSimone, "Sunscreen and Suntan Products", *Handbook of Nonprescription Drugs.* 7th Ed., Chapter 26, pp. 499–511 (American Pharmaceutical Association, Washington, D.C.; 1982); Grove and Forbes, "A Method for Evaluating the Photoprotection Action of Sunscreen Agents Against UV-A Radiaion", *International Journal of Cosmetic Science,* 4, pp. 15–24 (1982); and U.S. Pat. No. 4,387,089, DePolo, issued June 7, 1983; the disclosures of all of which are incorporated herein by reference. Hence, although the immediate effects of ultraviolet radiation may be cosmetically and socially gratifying, the long-term hazards are cumulative and potentially serious.

The fact that these effects are taken seriously by the general public is suggested by considering the sun protection products' market. This market has grown considerably in recent years and many new products are introduced each year. What used to be looked upon as a seasonal business is no longer. Sun protection compounds are now included in a diversity of personal care products, particularly cosmetic-type products which are worn on a daily basis.

Sunblock agents are commercially available to protect the skin from UV radiation. These agents scatter or reflect ultraviolet radiation. Examples include titanium dioxide and zinc oxide. However, compositions containing these agents are opaque, generally unattractive in color, and are viewed as unacceptable for usage on more than just the nose or tops of the ears. Furthermore, these agents are very susceptible to rub-off or wear-off resulting in little or no protection.

The most common agents for sun protection are sunscreens. These agents exert their effects through chemical means, i.e., they absorb ultraviolet radiation so that it cannot penetrate the skin. Sunscreens present the user with several problems. For example, they must be on the surface of the skin at the time of exposure to be effective. Sunscreens are preventative so one must anticipate being in the sun. To be most effective, sunscreens must be on the skin as a continuous uniform film. Delivering such a film to the surface of the skin is very difficult; maintaining the film over time is almost impossible. Sunscreens must remain on the surface of the skin during exposure. However, sunscreens are easily rubbed off or washed off by sweating or swimming and can also be lost be penetration into the skin.

To overcome these problems, polymers such as ethyl cellulose, polyvinyl stearate, polyvinyl pyrollidone and eicosene copolymers have been used; however these polymers have not proved entirely satisfactory Further, sunscreen compositions containing acrylic acid copolymers have also been disclosed in U.S. Pat. No. 4,663,157 to Brock, issued May 5, 1987.

It is therefore an object of the present invention to provide a topical composition in a stable form, the use of which will prevent both acute (erythema) and chronic (photoaging) effects of exposure to the sun.

It is also an object of the present invention to provide a topical composition and a method for preventing these deleterious effects of the sun without interfering with the tanning response.

It is further an object of the present invention to provide a photoprotection composition with improved aesthetics which adheres to the skin and which is less susceptible to rub-off, wear-off or wash-off without the need for polymeric substantivity aids.

It is a still further object of the present invention to provide a photoprotection composition which can be applied to the skin in advance of UV exposure without significant loss of waterproofing efficacy.

These and other objects will become readily apparent from the detailed description that follows.

SUMMARY OF THE INVENTION

The present invention relates to a sunscreen composition having improved substantivity and moisture resistance for topical use comprising:
(a) from about 1% to about 20% of a sunscreen;
(b) from about 0.01% to about 5% of an emulsifier selected from the group consisting of alkyl substituted acrylic acid copolymers, TEA stearate salts, alkali neutralized mono- and di- alkyl phosphates including diethanolamine mono- and dicetyl phosphate and hydroxy cetyl phosphate and mixtures thereof;
(c) from about 0.1% to about 10% of a wax component having a required HLB of from about 1 to about 10 comprising: (i) an ester wax; and (ii) a wax selected from the group consisting of diester waxes and triglyceride waxes and mixtures thereof; and (d) a safe and effective amount of a topical carrier.

The present invention further relates to a method of inhibiting the deleterious effects of ultraviolet light exposure to skin comprising applying a safe and photoprotectively effective amount of these compositions.

All percentages and ratios used herein are by weight of the total composition and all measurements made at 25.C, unless otherwise designated.

DETAILED DESCRIPTION OF THE INVENTION

In accordance with the present invention, moisture resistant skin 10 treatment compositions, such as sunscreen and sun block formulations, and moisturizer formulations are provided, which compositions have improved moisture resistance and substantivity due to the presence therein of a specific wax component and are preferably in the form of a oil-in-water emulsion which contains water, emollients, emulsifiers, thickeners, preservatives, coloring agents, fragrances, antioxidants and the like and one or more known ultraviolet absorbing compounds (in the case of sunscreen or sun block formulations).

The formulation of the invention is preferably an oil-in-water type emulsion since this type of emulsion affords better cosmetic feel to the product. However, the product could also be formulated as a water-in-oil emulsion, cream base, or oil base. Depending upon the choice of ingredients, the formulation has a semi-solid cream-like consistency which can be packaged in a plastic squeeze tube or it has a lotion type consistency which can be packaged in a plastic squeeze container. The container can include a flow-type cap or pump-type dispenser.

Sunscreens. A wide variety of conventional sunscreening agents are suitable for use in the present invention. Segarin, et al., at Chapter VIII, pages 189 et seq., of *Cosmetics Science and Technology*, disclose numerous suitable agents. Specific suitable sunscreening agents include, for example: p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, -phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naphtholsulfonates (sodium salts of 2-naphthol3,6-disulfonic and of 2-naphthol-6,8-disulfonic acids); Dihydroxy-naphthoic acid and its salts; o- and p-Hydroxybiphenyldisulfonates; Coumarin derivatives (7-hydroxy, 7-methyl, 3- <phenyl); Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzene, Sulisbenzone, Dioxybenzone, Benzoresorcinol, 2,2',4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane.

Of these, 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)]aminobenzoate, 2-ethylhexyl2-cyano-3,3-diphenylacrylate, 2-ethylhexysalicylate, glyceryl p-aminobenzoate, 3,3,5-trimethylcyclohexysalicylate, methylanthranilate, p-dimethylaminobenzoic acid or aminobenzoate, 2-ethylhexyl p-dimethylamino benzoate, 2-phenylbenzimidazole-5-sulfonic acid 2-(p-dimethylaminophenyl)-5-sulfonicbenzoxazoic acid and mixtures of these compounds, are particularly useful.

Preferred sunscreens useful in the compositions of the present invention are 2-ethylhexyl p-methoxycinnamate, butylmethoxydibenzoylmethane, 2-hydroxy-4-methoxybenzophenone, octyldimethyl p-aminobenzoic acid, 2,2' dihydroxy-4-methoxybenzophenone and ethyl hexyl salicylate and mixtures thereof.

A safe and photoprotectively effective amount of sunscreen may be used in the sunscreen compositions of the present invention. By "safe and photoprotectively" is meant an amount sufficient to provide photoprotection when the composition is applied not so much as to cause any side effects or skin reactions. Generally from about 1% to about 30%, preferably from about 2% to about 20% of the composition comprise a sunscreening agent. Exact amounts will vary depending upon the sunscreen chosen and the desired Sun Protection Factor (SPF).

SPF is a commonly used measure of photoprotection of a sunscreen against erythema. This number is derived from another parameter, the minimal erythemal dose (MED). MED is defined as the "lease exposure dose at a specified wavelength that will elicit a delayed erythema response". The MED indicates the amount of energy reaching the skin and the responsiveness of the skin to the radiation. The SPF of a particular photoprotector is obtained by dividing the MED of protected skin by the MED of unprotected skin. The higher the SPF, the more effective the agent in preventing sunburn. The SPF value tells how many times longer a person can stay in the sun with use of the sunscreen (compared to a person with unprotected skin) before that person will experience 1 MED. For example, utilizing a sunscreen with an SPF of 6 will allow an individual to stay in the sun six times longer before receiving 1 MED. As the SPF value of a sunscreen increases, the less chance exists for development of tanning of the skin. Commercially available sunscreening products have SPF values ranging from 2 to 50.

Also particularly useful in the present invention are sunscreens such as those disclosed in Sabatelli, U.S. patent application Ser. No. 054,085 (filed June 2, 1987) and Sabatelli et al., U.S. patent application Ser. No. 054,046 (filed June 2, 1987). The sunscreening agents disclosed therein have, in a single molecule, two- distinct chromophore moieties which exhibit different ultra-violet radiation absorption spectra. One of the chromophore moieties absorbs predominantly in the UVB radiation range and the other absorbs strongly in the UVA radiation range.

These sunscreening agents provide higher efficacy, broader UV absorption, lower skin penetration and longer lasting efficacy relative to conventional sunscreens.

Preferred members of this class of sunscreening agents are 4-N,N-(2-ethylhexyl)methylaminobenzoic acid ester of 2,4-dihydroxybenzophenone; N,N-di-(2-ethylhexyl)-4-aminobenzoic acid ester with 4-hydroxydibenzoylmethane; 4-N,N(2-ethylhexyl) methylaminobenzoic acid ester with 4-hydroxydibenzoylmethane; 4-N,N-(2-ethylhexyl)methylaminobenzoic acid ester of 2-hydroxy-4-(2-hydroxyethoxy)benzophenone; 4-N,N-(2-ethylhexyl) methylaminobenzoic acid ester of 4-(2-hydroxyethoxy)dibenzoylmethane; N-N-di-(2-ethylhexyl)-4-aminobenzoic acid ester of 2-hydroxy-4-(2-hydroxyethoxy)benzophenone, and N,N-di-(2-ethylhexyl)4-aminobenzoic acid ester of 4-(2-hydroxyethoxy)dibenzoylmethane and mixtures thereof.

Emulsifier. The compositions of the present invention also essentially comprise at least one emulsifier. Preferred is the use of alkyl substituted acrylic acid copolymers comprising polymers of a monomeric mixture containing 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula

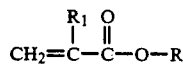

wherein R is an alkyl radical containing 10 to 30 carbon atoms and $R_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups.

Preferably, these polymers contain from about 96 to about 97.9 weight percent of acrylic acid and from about 2.5 to about 3.5 weight percent of acrylic esters wherein the alkyl group contains 12 to 22 carbon atoms, and $R_1$ is methyl, most preferably the acrylate ester is stearyl methacrylate. Preferably, the amount of cross-linking monomer is from about 0.2 to 0.4 weight percent. The preferred crosslinking monomers are allyl pentaerythritol, trimethylolpropane diallylether or allyl sucrose. These polymers are fully described in U.S. Pat. No. 4,509,949, Huang et al., issued Apr. 5, 1985.

The carboxylic monomers useful in the production of polymers used in this invention are the olefinically-unsaturated carboxylic acids containing at least one activated carbon-to-carbon olefinic double bond, and at least one carboxyl group.

The preferred carboxylic monomers are the acrylic acids having the general structure:

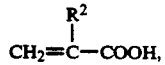

wherein $R^2$ is a substituent selected from the class consisting of hydrogen, halogen, and the cyanogen (—C≡N) groups, monovalent alkyl radicals, monovalent alkaryl radicals and monovalent cycloaliphatic radicals. Of this class, acrylic, methacrylic, and ethacrylic acid are most preferred. Another useful carboxylic monomer is maleic anhydride or the acid. The amount of acid used will be from about 95.5 to about 98.9 weight percent of the total monomers used. More preferably the range will be from about 96 to about 97.9 weight percent.

The polymers are crosslinked with a polyfunctional vinylidene monomer containing at least 2 terminal $CH_2<$ groups, including for example, butadiene, isoprene, divinyl benzene, divinyl naphthlene, allyl acrylates, and the like. Particularly useful crosslinking monomers for use in preparing the copolymers are polyalkenyl polyethers having more than one alkenyl ether grouping per molecule. The most useful possess alkenyl groups in which an olefinic double bond is present attached to a terminal methylene grouping, $CH_2=C<$. Most preferred from this class is Carbomer 1342 (available as Carbopol 1342 from B. F. Goodrich).

Also useful are TEA stearate salts, alkali neutralized mono- and di- alkyl phosphates including diethanolamine mono- and di- cetyl phosphate (available from Givaudan as Amphisol) and hydroxy cetyl phosphate (available from Henkel as Forlanit E).

The emulsifiers used in the present invention should be dispersable (but not soluble) in water.

The emulsifier typically comprises in total from about 0.01% to about 5%, preferably from about 0.05% to about 3%, and most preferably from about 0.05% to about 1%, of the compositions of the present invention.

Wax Component. An essential component of the compositions herein is a wax component having a required HLB of from about 1 to about 10, preferably from about 1 to about 8, more preferably from about 1 to about 6 and most preferably from about 1 to about 5 comprising:

(i) an ester wax; and
(ii) a wax selected from the group consisting of diester waxes and triglyceride waxes and mixtures thereof.

Preferably, the ratio of (i) to (ii) ranges from about 10:1 to about 1:1, more preferably from about 5:1 to about 1:1 and most preferably from about 3:1 to about 1:1.

The HLB (short for "Hydrophile-Lipophile Balance") value system is fully described, and values for various materials are provided, in the publication *The HLB System, A Time-Saving Guide to Emulsifier Selection* (published by ICI Americas Inc., Wilmington, Del.; 1984), the disclosures of which are incorporated herein by reference in their entirety.

Useful ester waxes include $C_{10}$-$C_{40}$ alcohols esterified with $C_{10}$-$C_{40}$ fatty acid, diesters of $C_{10}$-$C_{40}$ fatty acids where the alcohol is propylene glycol, ethylene glycol, polyethylene glycol, polypropylene glycol, polyglycerin, or glycerin, triglycerides or diglycerides of $C_{10}$-$C_{40}$ fatty acids, pentaerythritol tri- ortetra- esters of $C_{10}$-$C_{40}$ fatty acids, $C_{10}$-$C_{40}$ fatty acids of sorbitan triesters, $C_{10}$-$C_{40}$ fatty acids of sucrose polyesters having 3-8 moles of substitution, myristyl myristate, paraffin, synthetic waxes such as Fischer-Tropsche waxes, microcrystalline waxes, castor wax, partially hydrogenated vegetable oils, behenyl behenrate and myristyl propionate and mixtures thereof.

Useful diester waxes include Synchrowax ERL-C (C18-36 acid glycolester) (available from Croda) and propylene glycol diester waxes including ethylene glycol distearate and glycol distearate. Useful triglyceride waxes include Shea Butter, Cocoa Butter, Synchrowax HGL-C (C18-36 acid triglyceride), Synchrowax HRC (tribehenin), Synchrowax HRS-C [tribehenin (and) calcium behenate] (all available from Croda Inc.), tristearin, trimyristate and fully hydrogenated vegetable oils and mixtures thereof. Preferred is a mixture of diester and triglyceride waxes in a ratio of from about 5:1 to about 1:1 and more preferably from about 4:1 to about 1:1.

Waxes useful in the compositions of this invention are disclosed in the following, all of which are incorporated by reference herein in their entirety: U.S. Pat. No. 4,049,792, to Elsnau, issued Sept. 20, 1977; U.S. Pat. No. 4,151,272, to Geary et al., issued Apr. 24, 1975; U.S. Pat. No. 4,229,432, to Geria, issued Oct. 21, 1980; U.S. Pat. No. 4,280,994, to Turney, issued Jul. 28, 1981; U.S. Pat. No. 4,126,679, to Davy et al., issued Nov. 21, 1978; and European Patent Application Publication Number 117,070, to May, published Aug. 29, 1984, "The Chemistry and Technology of Waxes", A. H. Warth, 2nd Edition, reprinted in 1960, Reinhold Publishing Corporation, pp. 391-393 and 421; "The Petroleum Chemicals Industry", R. F. Goldstein and A. L. Waddeam, 3rd Edition (1967), E & F.N. Span Ltd., pp 33-40; "The Chemistry and Manufacture of Cosmetics", M. G. DeNavarre, 2nd edition (1970), Van Nostrand & Company, pp 354-376; and in "Encyclopedia of Chemical Technology:, Vol. 24, Kirk-Othmer, 3rd Edition (1979) pp 466-481.

OPTIONAL COMPONENTS

Emollients. The compositions of the present invention preferably comprise at least one emollient. Preferred emollients are volatile silicone oils, non-volatile emollients, and the highly branched hydrocarbons known as the Permethyl 99 through 108A series (available from Permethyl Corporation) and mixtures thereof. The compositions of the present invention more preferably comprise at least one volatile silicone oil which functions as a liquid emollient, or especially in a mixture of volatile silicone oils and non-volatile emollients. The term "volatile", as used herein, refers to those materials which have a measurable vapor pressure at ambient temperature.

Volatile silicone oils useful in the compositions of the present invention are preferably cyclic. The following formula illustrates cyclic volatile polydimethylsiloxanes useful in the compositions disclosed herein:

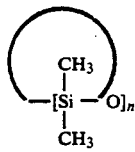

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C. while cyclic materials typically have viscosities of less than about 10 centistokes. A description of various volatile silicone oils is found in Todd, et al., "Volatile Silicone Fluids for Cosmetics", *Cosmetics & Toiletries.* 91. pages 27-32 (1976), the disclosures of which are incorporated by reference herein in their entirety.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by the Union Carbide Corp.); SF 1202 (manufactured by General Electric); and SWS-03314 (manufactured by SWS Silicones, Inc.).

The present compositions also preferably contain one or more non-volatile emollients. Such materials include fatty acid and fatty alcohol esters, hydrocarbons, non-volatile silicone oils, and mixtures *Cosmetics, Science and Technology* 27-104 (M. Balsam and E. Sagarin, Ed.; 1972), and U.S. Pat. No. 4,202,879, to Shelton, issued May 13, 1980 (both incorporated by reference herein).

Non-volatile silicone oils useful as an emollient material include polyalkylsiloxanes, polyalklyarylsiloxanes, and polyethersiloxane copolymers. The essentially non-volatile polyalkyl siloxanes useful herein include, for example, polydimethyl siloxanes with viscosities of from about 5 to about 100,000 centistokes at 25 C. Among the preferred non-volatile emollients useful in the present compositions are the polydimethyl siloxanes having viscosities from about 10 to about 400 centistokes at 25° C. Such polyalkyl siloxanes include the Vicasil series (sold by General Electric Company) and the Dow Corning 200 series (sold by Dow Corning Corporation). Polyalkylaryl siloxanes include polymethylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corporation). Useful polyether siloxane copolymers include, for example, a polyoxyalkylene ether copolymer having a viscosity of about 1200 to 1500 centistokes at 25° C. Such a fluid is available as SF-1066 organosilicone surfactant (sold by General Electric Company). Polysiloxane ethylene glycol ether copolymers are preferred copolymers for use in the present compositions.

Non-polar fatty acid and fatty alcohol esters useful herein as an emollient material include, for example, di-isopropyl adipate, isopropyl myristate, isopropyl palmitate, ethyl hexyl palmitate, isodecyl neopentanoate $C_{12}$-$C_{15}$ alcohol benzoate, diethyl hexyl maleate, PPG-14 butyl ether and PPG-2 myristyl ether propionate. Hydrocarbons such as isohexadecane (e.g., Permethyl 101A supplied by Presperse), petrolatum and USP light (e.g. Klearol ®) or heavy (e.g. Kaydl ®) mineral oils are also useful as emollients.

The emollients typically comprise in total from about 1% to about 50%, preferably from about 1% to about 25%, and more preferably from about 1% to about 10% by weight of the compositions of the present invention.

The following non-limiting examples illustrate embodiments of the subject invention wherein both essential and optional ingredients are combined. It is to be understood that these examples are for illustrative purposes only and are not to be construed as limiting the scope of the invention thereto.

EXAMPLE I

An oil-in-water emulsion prepared by combining the following components utilizing conventional mixing techniques.

| Components | A<br>% Weight | B<br>% Weight | C<br>% Weight |
| --- | --- | --- | --- |
| Water, purified | q.s. | q.s. | q.s. |
| Carbopol 1342 | 0.15 | 0.15 | 0.15 |
| Carbopol 934 | 0.30 | 0.20 | 0.20 |
| Escalol 507 (octyl dimethyl PABA) | 2.00 | 2.00 | 2.00 |
| Octyl Methoxycinnamate | 2.00 | 2.00 | 2.00 |
| Stearic Acid | 2.50 | 2.50 | 2.50 |
| $C_{12-15}$ alcohols benzoate | 10.00 | 10.00 | 10.00 |
| Myristyl myristate | 1.00 | 1.00 | 1.00 |
| Shea Butter | 1.00 | 1.00 | 1.00 |
| Triethanolamine 99% | 0.45 | 1.00 | 0.30 |
| Cyclomethicone | 2.00 | 2.00 | 2.00 |
| Propyl paraben | 0.20 | 0.20 | 0.20 |
| Methyl paraben | 0.30 | 0.30 | 0.30 |
| DMDM Hydantoin | 0.20 | 0.20 | 0.20 |
| Fragrance | 0.50 | 0.50 | 0.50 |
| Amphisol (DEA-cetyl phosphate) | — | — | 1.0 |

This emulsion is useful for topical application to inhibit damage caused by acute or chronic UV exposure. Use of an amount of this composition sufficient to deposit about 1.0 mg/cm$^2$ of the sunscreening agent to the skin prior to UV exposure is appropriate.

EXAMPLE II

An oil-in-water emulsion prepared by combining the following components utilizing conventional mixing techniques.

| Components | A<br>% w/w | B<br>% w/w |
| --- | --- | --- |
| Water, purified | q.s. | q.s. |
| Carbopol 1342 | 0.15 | 0.15 |
| Carbopol 934 | 0.20 | 0.20 |
| Octyl Dimethyl PABA | 8.00 | 8.00 |
| Octyl Methoxycinnamate | 4.00 | 4.00 |
| Benzophenone-3 | 4.00 | 4.00 |
| $C_{12-15}$ alcohols benzoate | 5.00 | 5.00 |
| Octyldodecyl Stearoyl Stearate | 5.00 | 5.00 |
| Castor Wax MP 70 | 2.00 | 2.00 |
| Cyclomethicone | 3.00 | 3.00 |
| Triethanolamine 99% | 0.35 | 0.60 |
| Synchrowax HRC | 2.00 | 2.00 |
| Propyl paraben | 0.15 | 0.15 |
| Methyl paraben | 0.20 | 0.20 |
| Benzyl alcohol | 0.30 | 0.30 |
| Fragrance | 0.50 | 0.50 |
| Hydrocetyl phosphate | — | 1.00 |

This emulsion is useful for topical application to inhibit damage caused by acute or chronic UV exposure. Use of an amount of this composition sufficient to deposit about 2.0 mg/cm$^2$ of the sunscreening agent to the skin prior to UV exposure is appropriate.

EXAMPLE III

An oil-in-water emulsion prepared by combining the following components utilizing conventional mixing techniques.

| Components | % w/w |
| --- | --- |
| Water, purified | q.s. |
| Carbopol 1342 | 0.15 |
| Carbopol 940 | 0.20 |
| Octyl Dimethyl PABA | 8.00 |
| Octyl Methoxycinnamate | 3.00 |
| Benzophenone-3 | 3.00 |
| Isostearyl Benzoate | 5.00 |
| Cocoa Butter | 2.00 |
| Behenyl Behenate | 3.00 |
| Triethanolamine 94% | 0.35 |
| Dimethicone (350 cts) | 2.00 |
| Propyl paraben | 0.20 |
| Methyl paraben | 0.35 |
| DMDM Hydantoin | 0.30 |
| Fragrance | 0.50 |

This emulsion is useful for topical application to inhibit damage caused by acute or chronic UV exposure. Use of an amount of this composition sufficient to deposit about 2.0 mg/cm$^2$ of the sunscreening agent to the skin prior to UV exposure is appropriate.

EXAMPLE IV

An oil-in-water emulsion prepared by combining the following components utilizing conventional mixing techniques.

| Components | % w/w |
| --- | --- |
| Water, purified | q.s. |
| Carbopol 1342 | 0.35 |
| Octyl Methoxycinnamate | 8.00 |
| Benzophenone-3 | 3.00 |
| Octyl Salicylate | 3.00 |
| Ethylene Glycol stearate | 0.50 |
| Synchrowax ERC (synthetic diester) | 3.00 |
| Tristearin | 2.00 |
| Triethanolamine 99% | 0.35 |
| Isostearyl benzoate | 10.00 |
| Octyldodecyl stearoyl stearate | 5.00 |
| Propyl paraben | 0.25 |
| Methyl paraben | 0.30 |
| Germall 115 | 0.30 |
| Fragrance | 0.80 |

This emulsion is useful for topical application to inhibit damage caused by acute or chronic UV exposure. Use of an amount of this composition sufficient to deposit about 2.0 mg/cm$^2$ of the sunscreening agent to the skin prior to UV exposure is appropriate.

EXAMPLE V

An oil-in-water emulsion prepared by combining the following components utilizing conventional mixing techniques.

| Components | % w/w |
| --- | --- |
| Water, purified | q.s. |
| Carbopol 1342 | 0.20 |
| Carbopol 940 | 0.10 |
| Octyl dimethyl PABA | 8.00 |
| Menthyl anthranilate | 5.00 |
| Cetyl palmitate | 3.00 |
| Ethylene Glycol Distearate | 3.00 |
| Isodecyl Neopentanoate (Dermol 105) | 2.00 |
| Triethanolamine 99% | 0.30 |
| Cyclomethicone (Dow Corning 344) | 1.50 |
| Propyl paraben | 0.15 |
| Methyl paraben | 0.20 |
| DMDM Hydantoin | 0.35 |
| Fragrance | 1.00 |

This emulsion is useful for topical application to inhibit damage caused by acute or chronic UV exposure. Use of an amount of this composition sufficient to deposit about 2.0 mg/cm$^2$ of the sunscreening agent to the skin prior to UV exposure is appropriate.

EXAMPLE VI

An oil-in-water emulsion prepared by combining the following components utilizing conventional mixing techniques.

| Components | % w/w |
| --- | --- |
| Water, purified | q.s. |
| Carbopol 934 | 0.20 |
| Carbopol 1342 | 0.15 |
| Disodium EDTA | 0.10 |
| Octyl dimethyl PABA | 2.00 |
| Octyl Methoxycinnamate | 2.00 |
| Isostearyl benzoate | 10.00 |
| Octyldodecyl stearoyl stearate | 5.00 |
| Myristyl myristate | 2.00 |
| Shea Butter | 2.00 |
| Ethylene Glycol stearate | 0.20 |
| Triethanolamine 99% | 0.35 |
| Cyclomethicone | 2.00 |
| Propyl paraben | 0.15 |
| Methyl paraben | 0.25 |
| Butylene Glycol | 2.00 |
| Benzyl alcohol | 0.30 |
| DMDM Hydantoin | 0.40 |
| Fragrance | 1.00 |

This emulsion is useful for topical application to inhibit damage caused by acute or chronic UV exposure. Use of an amount of this composition sufficient to deposit about 2.0 mg/cm$^2$ of the sunscreening agent to the skin prior to UV exposure is appropriate.

EXAMPLE VII

An oil-in-water emulsion prepared by combining the following components utilizing conventional mixing techniques.

| Components | % w/w |
| --- | --- |
| Water, purified | q.s. |
| Carbopol 1342 | 0.15 |
| Carbopol 940 | 0.15 |
| Octyl methoxycinnamate | 8.00 |
| Octyl salicylate | 3.00 |
| Benzophenone-3 | 3.00 |
| C$_{12-15}$ alcohols benzoate | 8.00 |
| Isodecyl Neopentanoate | 3.00 |
| Wecobee-m (Hydrogenated vegetable oil) | 3.00 |
| Satulan (Hydrogenated lanolin) | 2.00 |
| Synchrowax HGL | 3.00 |
| Dimethicone (350 cts) | 2.50 |
| Triethanolamine 99% | 0.30 |
| Glycerin | 2.00 |
| Propyl paraben | 0.20 |
| Methyl paraben | 0.30 |
| Germall 115 | 0.40 |

This emulsion is useful for topical application to inhibit damage caused by acute or chronic UV exposure. Use of an amount of this composition sufficient to deposit about 2.0 mg/cm$^2$ of the sunscreening agent to the skin prior to UV exposure is appropriate.

We claim:

1. An oil-in-water sunscreen emulsion composition having improved substantivity and moisture resistance for topical use comprising:

(a) from about 1% to about 40% of a sunscreen;

(b) from about 0.01% to about 5% of an emulsifier selected from the group consisting of alkyl substituted acrylic acid copolymers, TEA stearate salts, alkali neutralized monoalkyl phosphates, alkali neutralized dialkyl phosphates, hydroxy cetyl phosphate, and mixtures thereof, wherein said alkyl substituted acrylic acid copolymers comprise from about 95.9 to 98.8 weight percent of an olefinically unsaturated carboxylic monomer selected from the group consisting of acrylic, methacrylic and ethacrylic acids, about 1 to about 3.5 weight percent of an acrylate ester of the formula

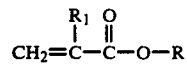

wherein R is an alkyl radical containing 10 to 30 carbon atoms and R$_1$ is hydrogen, methyl or ethyl, and 0.1 to 0.6 weight percent of a polymerizable cross-linking polyalkenyl polyether of a polyhydric alcohol containing more than one alkenyl ether group per molecule wherein the parent polyhydric alcohol contains at least 3 carbon atoms and at least 3 hydroxyl groups;

(c) from about 1% to about 60% of a wax component having a required HLB of from about 1 to about 10 comprising:

(i) an ester wax selected from the group consisting of C$_{10\text{-}40}$ alcohols esterified with C$_{10\text{-}40}$ fatty acids, diesters of C$_{10}$-C$_{40}$ fatty acids where the alcohol is propylene glycol, ethylene glycol or glycerin, polyethylene glycol, polypropylene glycol, polyglycerin, triglycerides or diglycerides of C$_{10\text{-}40}$ fatty acids, pentaerythritol tri- or tetra- esters of C$_{10\text{-}40}$ fatty acids, C$_{10\text{-}40}$ fatty acids of sorbitan triesters, C$_{10\text{-}40}$ fatty acids of sucrose polyesters having 3-8 moles of substitution, myristyl myristate, paraffin, synthetic Fischer-Tropsche waxes, microcrystalline waxes, castor wax, partially hydrogenated vegetable oils, behenyl behenrate, myristyl propionate and mixtures thereof; and (ii) a wax selected from the group consisting of diester waxes and triglyceride waxes and mixtures thereof wherein said diester wax is selected from the group consisting of C18-36 acid glycol ester and propylene glycol diester waxes and mixtures thereof, and wherein said triglyceride wax is selected from the group consisting of shea butter, cocoa butter, C18-36 acid triglyceride, tribehenin, tribehenin (and) calcium behenate, tristearin, trimyristate, fully hydrogenated vegetable oils, and mixtures thereof; and (d) a safe and effective amount of a topical carrier.

2. A sunscreen composition according to claim 1 wherein said wax component has a required HLB of from about 1 to about 8 and wherein the ratio of (i) to (ii) ranges from about 5:1 to about 1:1.

3. A sunscreen composition according to claim 2 wherein said wax component is present at a level of from about 5% to about 35% and wherein said emulsifier is present at a level of from about 0.05% to about 5%.

4. A sunscreen composition according to claim 3 wherein said sunscreen active is selected from the group consisting of 2-ethylhexyl p-methoxycinnamate, butylmethoxydibenzoylmethane, 2-hydroxy-4-methoxybenzophenone, 2,2' dihydroxy-4-methoxybenzophenone and ethyl hexyl salicylate, octyldimethyl p-aminobenzoic acid, the 4-N,N-(2-ethylhexyl)methylaminobenzoic acid ester of 2,4-dihydroxybenzophenone, the N,N-di-(ethylhexyl)-4-aminobenzoic acid ester of 4-hydroxydibenzoylmethane, the 4-N,N-(2-ethylhexyl)methylaminobenzoic acid ester of 4-hydroxydibenzoylmethane, the 4-N,N-(2-ethylhexyl)methylaminobenzoic acid ester of 2hydroxy-4-(2-hydroxyethoxy) benzophenone, the 4-N,N-(2-ethylhexyl)-methylaminobenzoic acid ester of 4-(2-hydroxyethoxy) dibenzoylmethane, the N-N-di-(2-ethylhexyl)-4-aminobenzoic acid ester of 2-hydroxy-4-(2-hydroxyethoxy)benzophenone, or the N.N-di-(2-ethylhexyl)-4-aminobenzoic acid ester of 4-(2-hydroxyethoxy)dibenzoylmethane and mixtures thereof.

5. A sunscreen composition according to claim 3 wherein said sunscreen active is selected from the group consisting of 2-ethylhexyl p-methoxycinnamate, butyl-methoxydibenzoylmethane, 2-hydroxy 4-methoxybenzophenone, octyldimethyl p-aminobenzoic acid and mixtures thereof.

6. A sunscreen composition according to claim 5 which further comprises from about 10% to about 50% of an emollient.

7. A sunscreen composition according to claim 6 wherein said emollient is selected from the group consisting of petrolatum, lanolin, tocopheryl acetate, USP light mineral oil, USP heavy mineral oil, isohexadecane, isodecyl neopentanoate, and mixtures thereof.

8. A sunscreen composition according to claim 7 which further comprises from about 0.01 to about 15% of an emulsifier.

9. A method for protecting the skin of humans or lower animals from the effects of ultraviolet radiation, said method comprising topically applying to the skin of the human or lower animal an effective coating of a sunscreen composition according to claim 10. A method for protecting the skin of humans or lower animals from the effects of ultraviolet radiation, said method comprising topically applying to the skin of the human or lower animal an effective coating of a sunscreen composition according to claim 2.

11. A method for protecting the skin of humans or lower animals from the effects of ultraviolet radiation, said method comprising topically applying to the skin of the human or lower animal an effective coating of a sunscreen composition according to claim 3.

12. A method for protecting the skin of humans or lower animals from the effects of ultraviolet radiation, said method comprising topically applying to the skin of the human or lower animal an effective coating of a sunscreen composition according to claim 4.

13. A method for protecting the skin of humans or lower animals from the effects of ultraviolet radiation, said method comprising topically applying to the skin of the human or lower animal an effective coating of a sunscreen composition according to claim 5.

14. A method for protecting the skin of humans or lower animals from the effects of ultraviolet radiation, said method comprising topically applying to the skin of the human or lower animal an effective coating of a sunscreen composition according to claim 6.

15. A method for protecting the skin of humans or lower animals from the effects of ultraviolet radiation, said method comprising topically applying to the skin of the human or lower animal an effective coating of a sunscreen composition according to claim 7.

* * * * *

UNITED STATES PATENT AND TRADEMARK OFFICE
CERTIFICATE OF CORRECTION

PATENT NO. : 5,219,558
DATED : June 15, 1993
INVENTOR(S) : Frederick W. Woodin, Jr. and George E. Deckner It is certified that error appears in the above-identified patent and that said Letters Patent is hereby corrected as shown below:

At column 1, line 48 "*Drugs*. 7th" should read --*Drugs*, 7th--.

At column 1, line 52 "Radiaion" should read --Radiation--.

At column 2, line 28 "satisfactory Further" should read --satisfactory. Further--.

At column 2, line 61 "dicetyl, " should read --di- cetyl--.

At column 3, line 8 "25.C" should read --25°C--.

At column 3, line 13 "skin 10 treatment" should read --skin treatment--.

At column 3, line 58 "3- <phenyl" should read --3-phenyl--.

At column 4, line 31 "20% of the" should read --20%, of the--.

At column 4, lines 31-32 "composition comprise" should read --composition may comprise--.

At column 4, line 61 "two- distinct" should read --two distinct--.

At column 6, line 49 "acid, diesters" should read --acids, diesters--.

At column 6, line 53 "tri- ortetra- esters" should read --tri- or tetra- esters--.

At column 6, line 62 "glycolester" should read --glycol ester--.

At column 7, line 66 "*Toiletries*. 91. pages" should read --*Toiletries*, 91, pages--.

UNITED STATES PATENT AND TRADEMARK OFFICE
CERTIFICATE OF CORRECTION

PATENT NO. : 5,219,558
DATED : June 15, 1993
INVENTOR(S) : Frederick W. Woodin, Jr. and George E. Deckner It is certified that error appears in the above-identified patent and that said Letters Patent is hereby corrected as shown below:

At column 8, line 11 "mixtures *Cosmetics*" should read --mixtures thereof. Emollients among those useful herein are described in *Cosmetics*--.

At column 8, line 21 "25 C" should read --25°C--.

At column 8, line 51 "Kaydl®" should read --Kaydol®--.

At column 9, line 24 "1.0 mg/cm$^2$" should read --2.0 mg/cm$^2$--.

At column 13, line 2 "2hydroxy" should read --2-hydroxy--.

At column 13, line 31 "according to claim" should read --according to claim 1--.

Signed and Sealed this

Thirtieth Day of March, 1999

Attest:

Q. TODD DICKINSON

*Attesting Officer*　　　*Acting Commissioner of Patents and Trademarks*